(12) United States Patent
Fraser et al.

(10) Patent No.: US 11,298,479 B2
(45) Date of Patent: Apr. 12, 2022

(54) AEROSOL DELIVERY DEVICE

(71) Applicant: Nicoventures Holdings Limited, London (GB)

(72) Inventors: Rory Fraser, London (GB); Siddhartha Jain, London (GB)

(73) Assignee: Nicoventures Trading Limited, London (GB)

( * ) Notice: Subject to any disclaimer, the term of this patent is extended or adjusted under 35 U.S.C. 154(b) by 671 days.

(21) Appl. No.: 16/308,623

(22) PCT Filed: May 19, 2017

(86) PCT No.: PCT/GB2017/051406
§ 371 (c)(1),
(2) Date: Dec. 10, 2018

(87) PCT Pub. No.: WO2017/216516
PCT Pub. Date: Dec. 21, 2017

(65) Prior Publication Data
US 2019/0150520 A1 May 23, 2019

(30) Foreign Application Priority Data

Jun. 13, 2016 (GB) ...................................... 1610220

(51) Int. Cl.
*A24F 47/00* (2020.01)
*A61M 15/06* (2006.01)
(Continued)

(52) U.S. Cl.
CPC ........... *A61M 15/06* (2013.01); *A24F 40/485* (2020.01); *A24F 40/51* (2020.01); *A61M 11/042* (2014.02);
(Continued)

(58) Field of Classification Search
CPC .... A61M 51/06; A61M 11/042; A61M 15/06; A24F 47/008
See application file for complete search history.

(56) References Cited

U.S. PATENT DOCUMENTS

| 5,060,671 A | 10/1991 | Counts |
| 5,095,921 A | 3/1992 | Losee |
(Continued)

FOREIGN PATENT DOCUMENTS

| CA | 2257618 | 7/2006 |
| CL | 2016002407 U1 | 5/2017 |
(Continued)

OTHER PUBLICATIONS

Extended European Search Report for Application No. 20167756.4, dated Jun. 29, 2020, 15 pages.
(Continued)

*Primary Examiner* — Neil Abrams
(74) *Attorney, Agent, or Firm* — Patterson Thuente Pedersen, P.A.

(57) ABSTRACT

An aerosol delivery device including a mouthpiece end; an aerosol generation chamber in fluid communication with the mouthpiece end via a primary air channel, wherein the aerosol generation chamber comprises an aerosol source for generating an aerosol from a source material for inhalation by a user through the mouthpiece end during use; and a sensor for detecting when a user inhales on the mouthpiece end, wherein the sensor is in fluid communication with the mouthpiece end via a secondary air channel, and wherein the sensor is located further from the mouthpiece end than the aerosol source, and the secondary air channel bypasses the aerosol generation chamber.

15 Claims, 4 Drawing Sheets

(51) Int. Cl.
  *A61M 11/04* (2006.01)
  *A24F 40/485* (2020.01)
  *A24F 40/51* (2020.01)
  *A61M 16/00* (2006.01)
  *A24F 40/10* (2020.01)

(52) U.S. Cl.
  CPC ...... *A24F 40/10* (2020.01); *A61M 2016/0021* (2013.01); *A61M 2205/3653* (2013.01); *A61M 2205/8206* (2013.01)

(56) References Cited

U.S. PATENT DOCUMENTS

| | | | |
|---|---|---|---|
| 5,105,831 A | 4/1992 | Banerjee | |
| 5,865,186 A | 2/1999 | Volsey | |
| 7,913,688 B2* | 3/2011 | Cross | A61M 11/042 128/203.26 |
| 8,881,737 B2* | 11/2014 | Collett | A24F 40/46 131/273 |
| 10,136,676 B2 | 11/2018 | Newns | |
| 10,966,460 B2* | 4/2021 | Frisbee | A61M 11/042 |
| 2008/0092912 A1 | 4/2008 | Robinson | |
| 2011/0265806 A1 | 11/2011 | Alarcon | |
| 2013/0192615 A1 | 8/2013 | Tucker et al. | |
| 2013/0220315 A1 | 8/2013 | Conley | |
| 2014/0060556 A1 | 3/2014 | Liu | |
| 2014/0366898 A1 | 12/2014 | Monsees | |
| 2015/0216237 A1* | 8/2015 | Wensley | A24F 40/46 131/273 |
| 2015/0282527 A1 | 10/2015 | Henry | |
| 2015/0374035 A1 | 12/2015 | Sanchez et al. | |
| 2016/0331034 A1 | 11/2016 | Cameron | |
| 2017/0197043 A1 | 7/2017 | Buchberger | |
| 2019/0150520 A1* | 5/2019 | Fraser | A24F 40/485 |
| 2019/0343182 A1 | 11/2019 | Yilmaz | |

FOREIGN PATENT DOCUMENTS

| | | |
|---|---|---|
| CN | 103263083 | 8/2013 |
| CN | 203369386 | 1/2014 |
| CN | 204120221 | 5/2014 |
| CN | 203692550 | 7/2014 |
| CN | 203692552 | 7/2014 |
| CN | 203801735 | 9/2014 |
| CN | 104146352 | 11/2014 |
| CN | 203952419 | 11/2014 |
| CN | 103859605 | 6/2016 |
| EP | 0336458 | 10/1989 |
| EP | 0461281 | 12/1991 |
| EP | 2989912 | 3/2016 |
| EP | 3100621 | 12/2016 |
| EP | 3245885 | 11/2017 |
| EP | 3469925 A1 | 4/2019 |
| GB | 2524779 | 10/2015 |
| GB | 2524856 | 10/2015 |
| GB | 2529201 | 2/2016 |
| KR | 20150127616 A | 11/2015 |
| RU | 2411047 | 2/2011 |
| WO | WO 97/31721 | 9/1997 |
| WO | WO-9731712 A1 | 9/1997 |
| WO | WO-9748431 A2 | 12/1997 |
| WO | WO 2013/102613 A1 | 7/2013 |
| WO | WO 2013/102615 A1 | 7/2013 |
| WO | WO-2013116565 A1 | 8/2013 |
| WO | WO 2013/155645 | 10/2013 |
| WO | WO 2014/012906 | 1/2014 |
| WO | WO 2014/012907 | 1/2014 |
| WO | WO2015120591 | 2/2014 |
| WO | WO-2015120588 A1 | 8/2015 |
| WO | WO-2015120636 A1 | 8/2015 |
| WO | WO 2016062777 | 4/2016 |
| WO | WO 2016/066635 | 5/2016 |
| WO | WO 2016/121143 | 8/2016 |
| WO | WO 2016/135342 | 9/2016 |
| WO | WO 2017/185051 | 10/2017 |
| WO | WO2018127417 | 7/2018 |
| WO | WO2018203044 | 11/2018 |
| WO | WO2018234792 | 12/2018 |

OTHER PUBLICATIONS

Office Action For Chilean Application No. 201803426, dated Dec. 30, 2020, 7 pages.
Office Action For Korean Application No. 10-2018-7036090, dated Dec. 22, 2020, 3 pages.
International Preliminary Report on Patentability, Application No. PCT/GB2017/051406, dated Jul. 25, 2018, 13 pages.
International Search Report and Written Opinion, Application No. PCT/GB2017/051406, dated Jul. 25, 2017, 16 pages.
Written Opinion of International Preliminary Examining Authority, Application No. PCT/GB2017/051406, dated May 14, 2018, 7 pages.
Russian Decision to Grant, Application No. 2018143938, dated Jun. 11, 2019, 12 pages.
India Examination Report, Application No. 201847046801, dated Jan. 13, 2020, 6 pages.
Japanese Office Action, Application No. 2018-561252, dated Jan. 27, 2020, 6 pages.
International Search Report and Written Opinion, Application No. PCT/EP2017/083785, dated Apr. 9, 2018, 14 pages.
International Search Report and Written Opinion, Application No. PCT/EP2017/083784, dated Jun. 20, 2018, 20 pages.
Ukrainian Office Action to Application No. a 2018 12020, dated Jun. 12, 2019, 5 pages.
Translated Ukrainian Office Action to Application No. a 2018 12020, dated Jun. 12, 2019, 5 pages.

* cited by examiner

AEROSOL DELIVERY DEVICE

PRIORITY CLAIM

The present application is a National Phase entry of PCT Application No. PCT/GB2017/051406, filed May 19, 2017, which claims priority from GB Patent Application No. 1610220.4, filed Jun. 13, 2016, each of which is hereby fully incorporated herein by reference.

FIELD

The present disclosure relates to aerosol delivery devices, in particular electronic cigarettes.

BACKGROUND

Aerosol provision systems/delivery devices such as e-cigarettes generally contain a reservoir of a source liquid containing a formulation, typically including nicotine, from which an aerosol is generated, such as through vaporization or other means. Thus an aerosol source for an aerosol provision system may comprise a heating element coupled to a portion of the source liquid from the reservoir, e.g. through capillary wicking. When a user inhales on the device, the heating element is activated to vaporize a small amount of the source liquid, which is thus converted to an aerosol for inhalation by the user. More particularly, such devices are usually provided with one or more air inlet holes located away from a mouthpiece end of the system. When a user sucks on the mouthpiece, air is drawn through the inlet holes and past the aerosol source. There is an air flow path connecting the inlet holes to the aerosol source and on to an opening in the mouthpiece so that air drawn past the aerosol source continues along the flow path to the mouthpiece opening, carrying some of the aerosol from the aerosol source with it. The aerosol-carrying air exits the aerosol provision system through the mouthpiece opening for inhalation by the user.

To enable "on-demand" provision of the aerosol, in some systems the air flow path is also in communication with an inhalation/puff sensor, such as a pressure sensor, e.g. based on a microphone. Inhalation by the user through the air flow path causes a drop in air pressure that is detected by the sensor, and an output signal from the sensor is used to generate a control signal for activating a supply of electrical power to the heating element, typically from a battery housed in the aerosol provision system. Hence, the aerosol is formed by vaporization of the source liquid in response to user inhalation through the device. At the end of the puff, the air pressure changes again, and this is also detected using the sensor and a control signal to stop the supply of electrical power is produced. In this way, the aerosol is generated only when required by the user.

In such a configuration the airflow path communicates with both the sensor and the heating element, which is itself in fluid communication with the reservoir of source liquid. Hence there is the possibility that source liquid can find its way to the sensor, for example if the e-cigarette is dropped, damaged or mistreated. Exposure of the sensor to liquid can stop the sensor from operating properly, either temporarily or permanently, which can be detrimental to performance.

Accordingly, approaches to mitigating this problem are of interest.

SUMMARY

According to an aspect of certain embodiments there is provided an aerosol delivery device comprising: a mouthpiece end; an aerosol generation chamber in fluid communication with the mouthpiece end via a primary air channel, wherein the aerosol generation chamber comprises an aerosol source for generating an aerosol from a source material for user inhalation through the mouthpiece end; and a sensor for detecting when a user inhales on the mouthpiece end, wherein the sensor is in fluid communication with the mouthpiece end via a secondary air channel, and wherein the sensor is located further from the mouthpiece end than the aerosol source, and the secondary air channel bypasses the aerosol generation chamber.

According to an aspect of certain other embodiments there is provided an aerosol delivery device that includes a mouthpiece end; an aerosol generation chamber in fluid communication with the mouthpiece end via a primary air channel, wherein the aerosol generation chamber comprises aerosol generation means for generating an aerosol from a source material for inhalation by a user through the mouthpiece end during use; and sensor means for detecting when a user inhales on the mouthpiece end, wherein the sensor means is in fluid communication with the mouthpiece end via a secondary air channel, and wherein the sensor means is located further from the mouthpiece end than the aerosol generation means, and the secondary air channel bypasses the aerosol generation chamber.

According to an aspect of certain other embodiments, there is provided an aerosol delivery device comprising an aerosol source for generating an aerosol from a source material for user inhalation through a mouthpiece end of the device, and a sensor for sensing when a user inhales on the mouthpiece end. The aerosol delivery device may be formed of a reusable part and a replaceable cartridge part, wherein the reusable part includes the sensor and the replaceable cartridge part includes the source material and the mouthpiece end. The replaceable part may further include a primary air channel for providing fluid communication between the aerosol source and the mouthpiece end of the device and a secondary air channel providing fluid communication between the sensor and the mouthpiece end when the replaceable cartridge is coupled to the reusable part in use.

It will be appreciated that features and aspects of the disclosure described above in relation to the first and other aspects of the disclosure are equally applicable to, and may be combined with, embodiments of the disclosure according to other aspects of the disclosure as appropriate, and not just in the specific combinations described above.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to (but is not limited to) aerosol delivery devices, such as electronic cigarettes (e-cigarettes). Throughout the following description the term "electronic cigarette" may sometimes be used; however, it will be appreciated this term may be used interchangeably with aerosol (vapor) delivery device/system.

Figure 1:
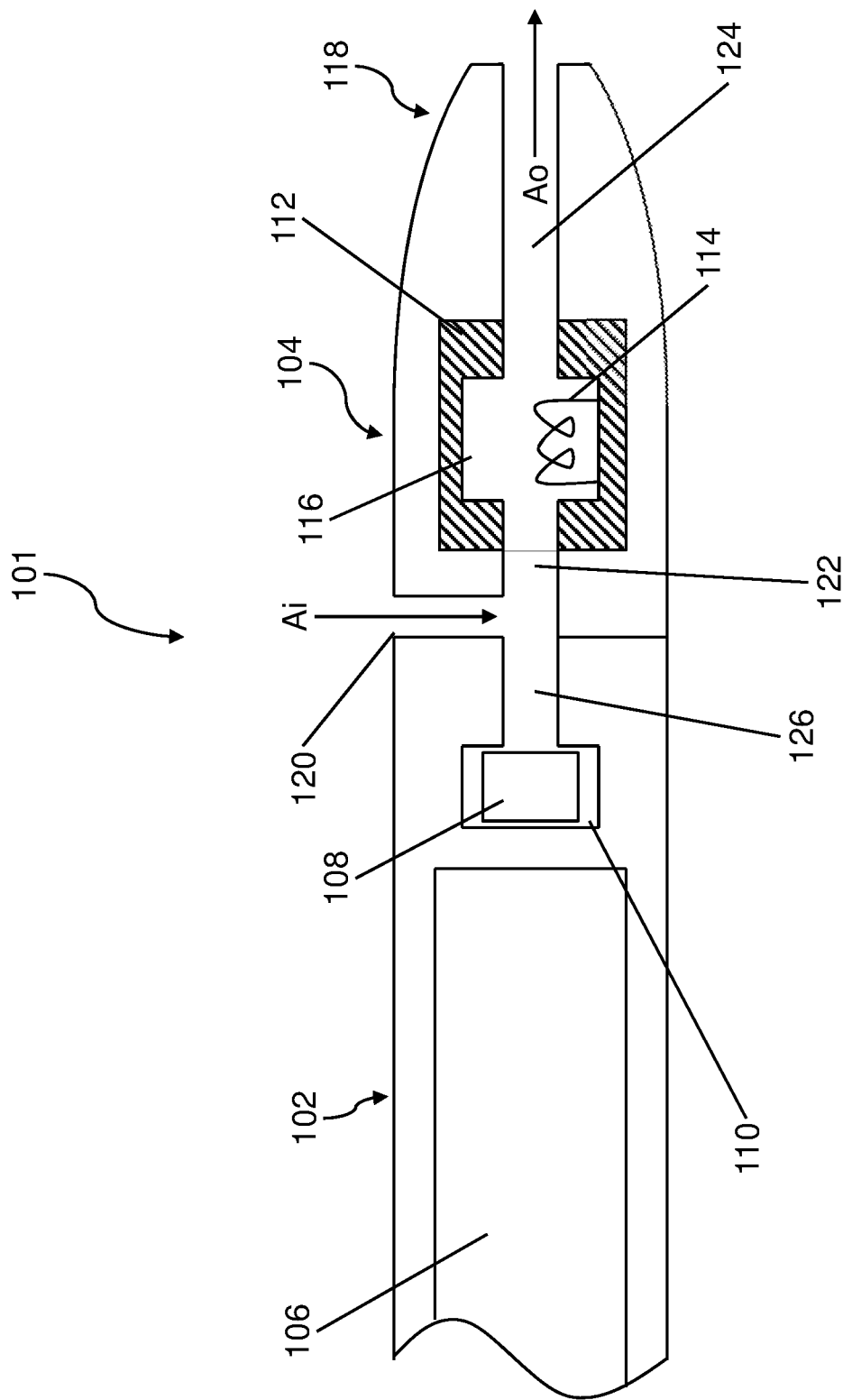
FIG. 1 schematically shows a cross sectional view of an exemplary configuration of an electronic cigarette.

FIG. 1 shows an example of some aspects of a conventional electronic cigarette 101. The electronic cigarette 101 shown in FIG. 1 is substantially cylindrical in shape and is a two-part device comprising a reusable part 102 and a replaceable cartridge/detachable part 104. The reusable part 102 and the detachable part 104 are separable to allow replacement of the detachable part 104, for example when a source of aerosol precursor material in the replaceable part 104 is exhausted, and are coupled together for normal use. The reusable part 102 generally includes components with operating lifetimes longer than the expected lifetime of the detachable/consumable part 104. The reusable part includes a battery 106 for supplying electric power to the electronic cigarette 101 as well as an inhalation sensor 108 housed in a sensor chamber 110. The reusable part 102 also comprises electronic circuitry (not shown) for controlling the operation of the electronic cigarette 101 as well as electrical contacts (not shown) positioned to connect with corresponding contacts on the detachable part 104 when the reusable part 102 and detachable part 104 are coupled together.

The detachable part 104 shown in FIG. 1 includes a liquid reservoir 112 containing a liquid to be vaporized and inhaled.

Typically a wicking material (not shown) is disposed in contact with liquid in or from the reservoir 112 in order to draw liquid from the liquid reservoir 112 to the vicinity of a heating element 114. The heating element 114 is positioned in close proximity to the wicking material so as to be able to sufficiently heat the liquid drawn to the heating element 114 by the wicking material. The heating element 114 may be a conductive wire that may be shaped into a coil. It is also known to provide the wick and heating element as a single structure, for example comprising a porous resistive element, for example formed from a metallic sheet or a non-metallic material with appropriate resistance and porosity characteristics. The heating element 114 and exposed part of the wicking material are disposed in a vaporization chamber 116 defining a zone into which the liquid is vaporized and an aerosol generated.

The detachable part 104 has a mouthpiece end 118 (shown generally to the right in FIG. 1) through which a user inhales on the device in normal use. FIG. 1 shows the mouthpiece end 118 having a curved surface that gradually decreases in diameter the further from the interface between the detachable part 104 and reusable part 102. This is just one example of a mouthpiece end 118 configuration; the mouthpiece end 118 may be a straight taper instead of curved, or the mouthpiece end 118 may maintain the same thickness along its length.

Generally, a detachable part 104 including a liquid reservoir 112, heating element 114 and mouthpiece end 118 is sometimes referred to as a cartomizer to reflect its function as both a cartridge of source material and a vaporizer. When the liquid reservoir 112 runs dry or if the user wishes to change the liquid for another flavor/type, then the detachable part 104 may be removed from the reusable part 102 and another detachable part 104 coupled to the reusable part 102 in its place.

The detachable part 104 shown in FIG. 1 includes an air flow path that comprises an air inlet 120, a first channel portion 122, the aerosol generation chamber 116, and a second channel portion 124. When a user inhales or sucks on the mouthpiece end 118 of the electronic cigarette 101, air from the environment enters the electronic cigarette 101 through the air inlet 120, as shown by arrow Ai in FIG. 1.

Air that enters the detachable part 104 via the air inlet 120 passes through the first channel portion 122 to the chamber 116. In the chamber 116 the air mixes with vaporized liquid from the heating element 114 to create an aerosol which is drawn along the second channel portion 124 towards the user's mouth for inhalation, as indicated by arrow Ao in FIG. 1.

As can also be seen in FIG. 1, the inhalation sensor chamber 110 of the reusable part 102 is in fluid communication with the first channel portion channel 122, and thus the heater chamber 116, via sensor channel 126.

As noted above, in use, a user places his or her mouth around the mouthpiece end 118 of the electronic cigarette 101 and begins inhaling. In addition to drawing air from the air inlet 120 as discussed above, the vacuum applied by the user creates a drop in pressure in the air flow path within the electronic cigarette. The inhalation sensor 108 in this example is a pressure sensor configured to detect the drop in pressure caused by the user inhaling on the mouthpiece end and output corresponding signaling to the control electronics of the electronic cigarette. When a drop in pressure greater than a predefined threshold is detected, the control electronics of the electronic cigarette is configured to activate the supply of power from the battery 106 to the heating element 114 to initiate vaporization of source liquid.

Thus, the electronic cigarette of FIG. 1 uses the inhalation sensor 108 to provide what is commonly referred to as "puff detection", whereby the heating element 114 is activated automatically in response to user inhalation, which increases user convenience.

In the electronic cigarette 101 shown in FIG. 1, it can be seen the inhalation sensor 108 is open to the air flow path through the electronic cigarette. The inventors have recognized a drawback of this configuration is the potential for liquid to flow from the liquid reservoir 112 into the inhalation sensor chamber 110, which can potentially damage the inhalation sensor 108 and other circuitry within the reusable part 102 connected to the inhalation sensor 108. This issue may arise for many different configurations, but may be particularly relevant for devices that store free liquid in a reservoir (i.e. devices which do not store the liquid formulation in an absorbent wadding material).

Figure 2:
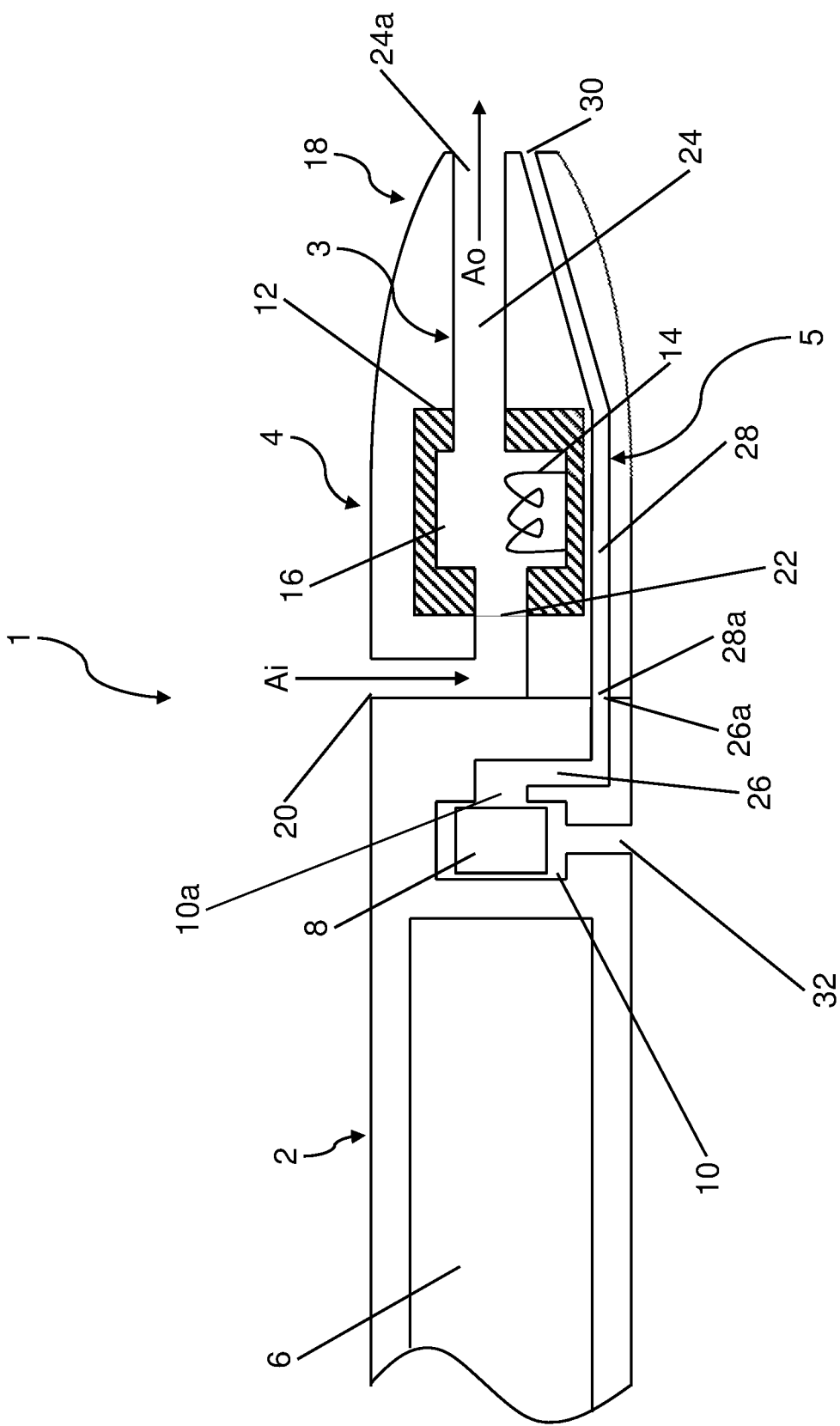
FIG. 2 schematically shows a cross sectional view of an aerosol delivery device in accordance with certain embodiments of the present disclosure.
Figure 3:
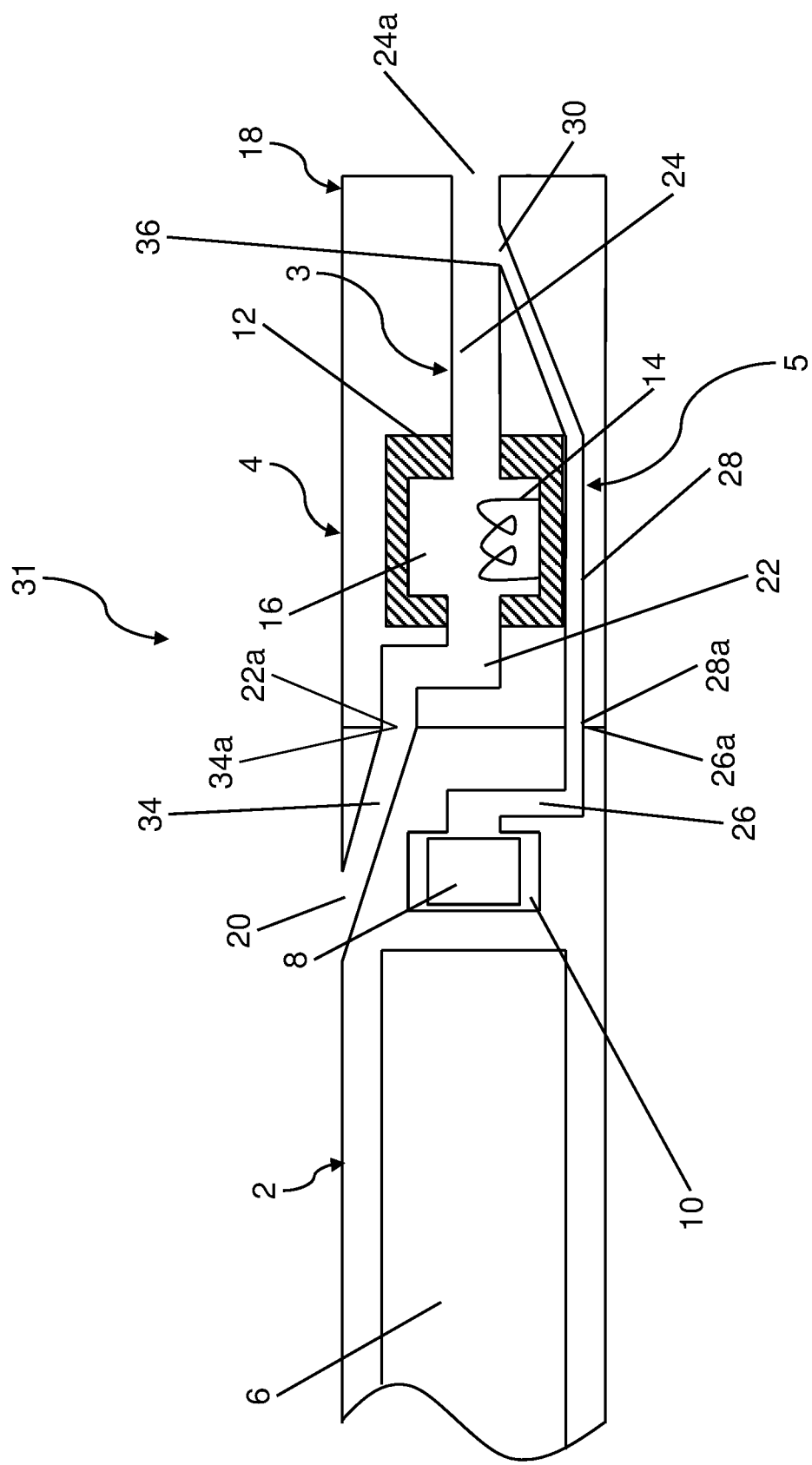
FIG. 3 schematically shows a cross sectional view of an aerosol delivery device in accordance with certain embodiments of the present disclosure.
Figure 4:
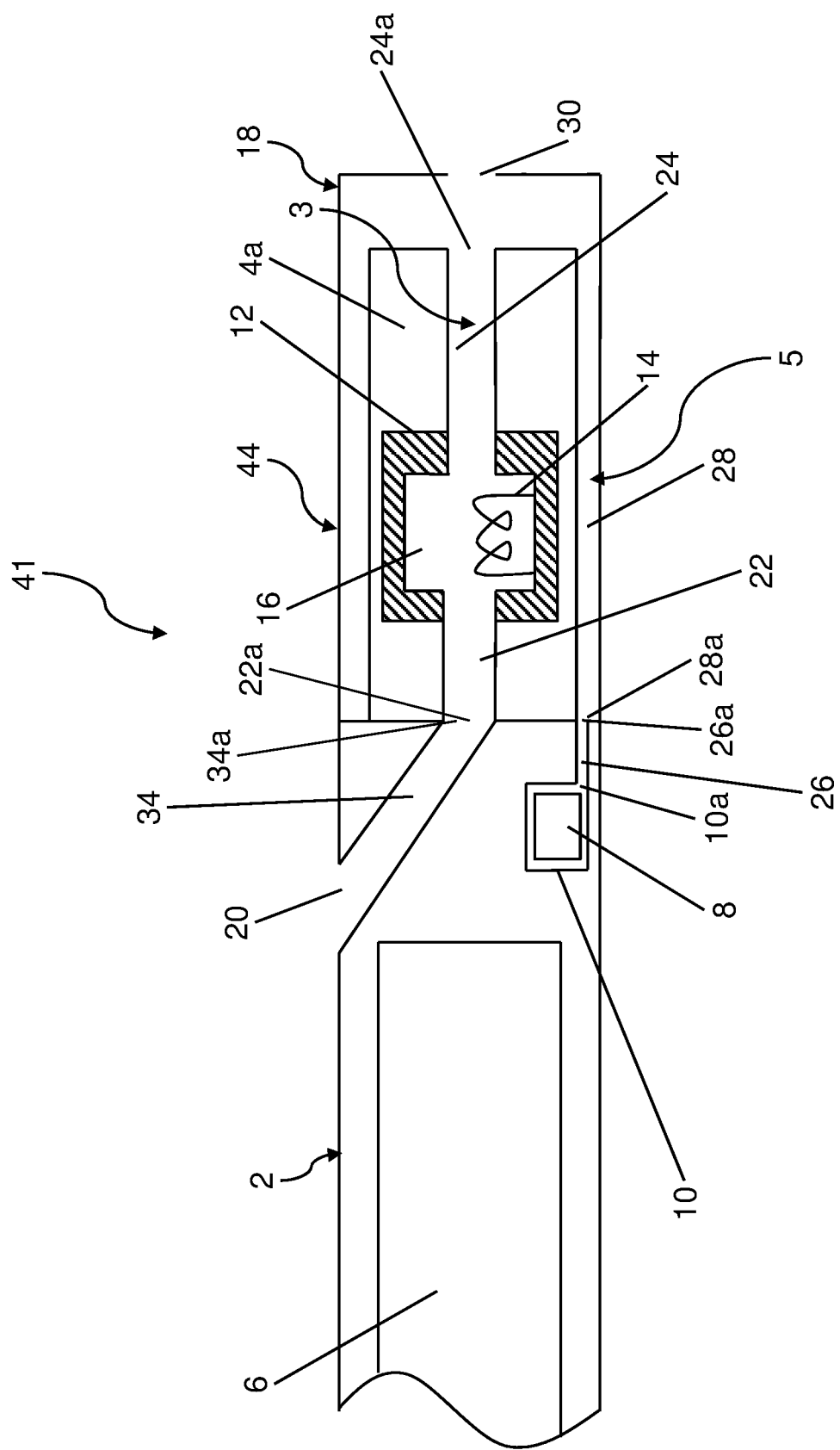
FIG. 4 schematically shows a cross sectional view of an aerosol delivery device in accordance with certain embodiments of the present disclosure.

FIG. 2 schematically shows one example of an electronic cigarette in accordance with an embodiment of the present disclosure which can help mitigate the issue noted above. FIGS. 3 and 4 show example implementations of an electronic cigarette in accordance with some other embodiments of the present disclosure. A number of aspects of the devices represented in FIGS. 2, 3 and 4 which are similar to corresponding aspects represented in the other figures are indicated by the same reference numeral. It will be appreciated that many aspects of the device that are represented in FIGS. 2, 3 and 4 are similar to, and will be understood from, corresponding elements of conventional devices, and in this regard, aspects of the various devices described herein which are not described in detail may implemented in accordance with conventional/established techniques.

FIG. 2 depicts an embodiment of an aerosol delivery device 1 according to the present disclosure. The aerosol delivery device 1 is to be understood as encompassing a range of different devices that are suitable for delivery of aerosol to a user based on vaporizing a liquid which can include medical inhalers or the like, but in some embodiments include electronic smoking articles such as electronic cigarettes.

The aerosol delivery device 1 comprises two parts; a reusable part 2 and a detachable/replaceable cartridge part 4, which are separable but coupled together when in use. The aerosol delivery device 1 may be cylindrical or substantially cylindrical in shape, and may have one or more tapered portions if desired. However, it should be noted that the device 1 may be formed of one part or any number of parts that may be interlinked with one another and may further adopt other shapes.

The reusable part 2 of FIG. 2 comprises a power source 6, an inhalation sensor 8, a sensor chamber 10, a sensor channel or first secondary air channel portion 26, and a sensor chamber air inlet 32.

The detachable/replaceable cartridge part 4 of FIG. 2 comprises an air inlet 20, a first primary air channel portion 22, an aerosol generation chamber 16 comprising a heating element 14 and a liquid reservoir 12, a second primary air channel portion 24, and a second secondary air channel portion 28. The detachable/replaceable cartridge part 4 of FIG. 2 also comprises a mouthpiece end 18 as well as an opening 24a and an opening 30 at the mouthpiece end 18.

The first primary air channel portion 22, the inner volume of the aerosol generation chamber 16, and the second primary air channel portion 24 collectively form a primary air channel 3. The primary air channel 3 in the device of FIG. 2 is defined from the air inlet 20 to the opening 24a in the mouthpiece end 18.

Additionally, when the reusable part 2 is coupled to the detachable/replaceable cartridge part 4, the sensor chamber air inlet 32, the sensor chamber 10, the first secondary air channel portion 26, and the second secondary air channel portion 28 collectively form a secondary air channel 5. The secondary air channel 5 in the device of FIG. 2 is defined from the sensor chamber air inlet 32 to the opening 30 in the mouthpiece end 18.

Any means of coupling may be employed in order to couple the reusable and detachable parts 2, 4. In one embodiment, the detachable part 4 may be provided with a threaded outer surface at one end thereof, while the reusable part 2 may be provided with an annular projection coaxial with the longitudinal axis of the reusable part 2. The annular projection may be provided with a threaded inner surface for receiving the threaded outer surface of the detachable part 4. In another embodiment, the detachable part 4 may comprise the annular projection and internal threaded surface to receive an outer threaded surface of the reusable part 2. In other configurations, the reusable part 2 and detachable part 4 may be coupled by other mechanisms, for example bayonet or snap-fittings.

One or more seal members may be disposed between the reusable and detachable/replaceable cartridge parts 2, 4 to provide air-tight coupling between the two parts 2, 4. Each of the detachable part 4 and reusable part 2 has end surfaces that are positioned in close proximity to one another or, in some cases, contact each other when the two parts 2, 4 are coupled in use—as seen in FIG. 2, for example. These surfaces define an interface and may be referred to as interface surfaces of the detachable part 4 and reusable part 2, respectively.

The reusable part 2 comprises the inhalation sensor 8 housed in the sensor chamber 10. The sensor 8 is any sensor capable of detecting when a user inhales on a mouthpiece end 18 of the detachable part 4. In some configurations, the sensor 8 may be a pressure sensor, for example based on a microphone, adapted to measure the pressure within the sensor chamber 10. Herein the sensor 8 shall be understood to refer to the mechanism for sensing pressure changes and/or airflow in response to a user puffing on the device, as well as electrical contacts and circuitry associated with the physical mechanism for sensing for generating an output signal indicative of when a user is inhaling on the device. In the device of FIG. 2, the sensor 8 is shown at a position close to the interface surface of the reusable part 2; however, the sensor 8 may be located at any position within the reusable part 2, e.g., at a distal end not shown in the Figure, with an appropriate extension of the fluid communications path to the sensor 8.

The power source 6 is also housed in the reusable part 2 and is configured to provide power to control circuitry of the device and the sensor 8 as well as the heating element 14. The power source 6 may be a battery, such as a rechargeable battery. Any rechargeable battery such as nickel cadmium (NiCd), nickel metal hydride (NiMH), lithium ion (Li-ion), and lithium ion polymer (Li-ion polymer) may be used. The reusable part 2 may comprise electrical contacts on an external surface, such as the distal end of the reusable part 2 not shown in FIG. 2, for connecting to a charging port or the like for recharging the power source 6. This may include a USB port or similar connection.

The reusable part 2 comprises electrical contacts (not shown) for contacting with mutually corresponding electrical contacts (also not shown) on the detachable part 4 to couple electrical power across the interface between the two parts 2, 4 in order to supply power from the power source 6 to the detachable part 4, specifically to the heating element 14 thereof. Thus the electrical contacts on the detachable part 4 are electrically connected to the heating element 14, while the electrical contacts on the reusable part 2 are electrically connected to the control circuitry of the reusable part 2.

The liquid reservoir 12 containing a liquid to be vaporized (source material/aerosol precursor) is provided in the detachable part 4. The liquid may be any suitable liquid that can be vaporized for user inhalation. In one embodiment, the liquid comprises around 1 to 3% nicotine and 50% glycerol, with the remainder comprising roughly equal measures of water and propylene glycol, and possibly also comprising other components, such as flavorings. However, suitable liquids may alternatively include medicaments that may be inhaled in vapor form. The liquid reservoir 12 is provided with or adjacent to a wicking material which acts to wick liquid from the liquid reservoir 12 towards the heating element 14 under capillary force.

The heating element 14 is disposed in the aerosol generation chamber 16 of the detachable part 4. When the heating element 14 is active, the liquid from the liquid reservoir 12 held in the wicking material in the vicinity of the heating element 14 is vaporized. In one configuration, the heating element 14 comprises a conductive wire shaped into a coil wrapped around a portion of the wicking material to help ensure appropriate heat transfer to the liquid held by the wicking material. Alternatively, the heating element 14 may be provided in close proximity to, rather than wound around, the wicking material. More generally, it will be appreciated there are many different vapor generation technologies that may be employed in aerosol provision systems, and although a specific example is described herein with reference to a coil and wick arrangement for the sake of providing a concrete example, the principles described herein regarding the operation and arrangement of an inhalation sensor in accordance with certain embodiments of the disclosure can be applied in the same way regardless of the underlying vapor generation technology employed. That is to say, the principles described herein can be used in relation to puff/inhalation detection in any aerosol provision system, and are not restricted to aerosol provision systems reliant on a coil/wick configuration, but can be applied equally to other vaporization technologies, such as combined heater and wick configuration, for example based around a porous resistive material, such as a steel mesh, in contact with a liquid reservoir, or indeed in aerosol provision systems that do not employ an electrical heater.

The wicking material and heating element 14 may together be considered to comprise an aerosol source for generating an aerosol from a source material, such as the liquid contained in the liquid reservoir 12. However, as noted above, other components and/or technologies may be provided for generating an aerosol. The aerosol generation chamber 16 contains the aerosol source and defines the region/zone in which vaporized fluid mixes with airflow through the device to generate the aerosol for use inhalation.

The detachable part 4 includes the mouthpiece end 18. In FIG. 2 this is schematically shown as a tapered end that becomes progressively thinner in a thickness or height direction (and/or width direction) of the device 1. This may be in a curved manner, as shown in FIG. 2, or in a linear manner. Additionally, the thickness or height of the device 1 may remain approximately constant as shown in FIG. 3. In any case, the mouthpiece end 18 is configured so as to be comfortably received in a user's mouth.

In the embodiment shown in FIG. 2, the detachable part 4 comprises a cartridge which includes the mouthpiece end 18 in addition to the aerosol generation chamber 16. That is, the mouthpiece end 18 and aerosol generation chamber 16 are integrally provided in the cartridge. However, as seen in FIG. 4, there are other configurations for the device 1 which may include a separable and reusable mouthpiece cap 44 that defines the mouthpiece end 18 while a separate replaceable/disposable/consumable cartridge part **4*a* is provided that includes the aerosol source and aerosol generation chamber 16. It should also be appreciated that in some embodiments the aerosol source may be separable from the aerosol generation chamber 16**, for example for cleaning or replacement.

In broad summary, in accordance with some example implementations, the present disclosure proposes an aerosol delivery device 1 that provides separated air paths for the inhalation sensor 8 and the aerosol generation chamber 16, that is to say, in accordance with certain example implementations, the air path for the inhalation chamber bypasses the aerosol generation chamber 16.

The primary air channel 3 is provided to allow air (Ai) from the environment to be drawn into the aerosol generation chamber 16 for mixing with vaporized liquid from the aerosol source through the air inlet 20, and for allowing output air (Ao) including the vaporized liquid to exit the device into the user's mouth via the opening **24*a***.

The primary air channel 3 in FIG. 2 includes the air inlet 20, the first primary air channel portion 22, the aerosol generation chamber 16, the second primary air channel portion 24 and the opening **24*a*. In the particular embodiment shown in FIG. 2, the primary air channel 3 does not pass through the reusable part 2 but is defined only within the detachable part 4 (i.e. the air inlet 20 is provided in the detachable part 4**).

It should be noted that while only one air inlet 20 is shown in FIG. 2 by way of a schematic example, in some implementations a plurality of interconnected air inlets 20 may be provided. This means that a plurality of first primary air channel portions 22 may be provided in correspondence with the plurality of air inlets 20. More generally, it will be appreciated the air channels portions represented in the drawings and discussed herein are presented highly schematically for ease of representation and not necessarily representative of a particular structural implementation.

In accordance with the principles of the disclosure, the aerosol generation chamber 16 is in fluid communication with the mouthpiece end 18, and in particular the aerosol outlet opening **24*a*, via the primary air channel 3. In the example of FIG. 2, this fluid communication is provided by the second primary air channel portion 24 connecting between the aerosol generation chamber and the aerosol outlet 24*a*. A pressure drop at the aerosol outlet 24*a* caused by a user inhaling on the mouthpiece end 18 thus causes air to be drawn in through the air inlet 20 and along the primary air channel 3 to the user's mouth, picking up vaporized source liquid in the aerosol generation chamber 16** on the way.

The secondary air channel 5 fluidly connects the sensor 8 in the sensor chamber 10 to the mouthpiece end 18 of the detachable part 4, and in particular to secondary air channel opening 30. The secondary air channel 5 runs through both the reusable part 2 and the detachable part 4 in this example implementation.

The secondary air channel 5 thus comprises the first secondary air channel portion 26 and the second secondary air channel portion 28. The second secondary air channel portion 28 is provided in the detachable part 4 and terminates at the opening 30 at the mouthpiece end 18.

The first secondary air channel portion 26 extends from an opening **10*a* into the sensor chamber 10 to an opening 26*a* at the interface surface of the reusable part 2. The second secondary air channel portion 28 extends from an opening 28*a* provided at the interface surface of the detachable part 4 to the opening 30 at the mouthpiece end 18. Thus, when the reusable part 2 and detachable part 4 are assembled for use, the respective interface openings 26*a* and 28*a* of the first and second portions of the secondary air channel 5 align to provide fluid communication between the inhalation sensor 8 and the opening 30 at the mouthpiece end 18 of the device 1**.

In some example implementations the sensor chamber 10 may open directly to the interface surface of the reusable part 2, that is to say the first secondary air channel portion 26 may in effect be removed.

Thus, when a user wishes to start using the device 1 and puffs on the mouthpiece end 18, the sensor 8 detects the corresponding drop of pressure at the opening 30 to the secondary air channel 5 and provides an output signal to trigger activation of the heating element 14 by the device's control circuitry. Likewise, when a user stops puffing on the mouthpiece end 18, the sensor 8 senses the corresponding rise in pressure at the opening 32 of the secondary air channel 5 and provides an output signal to trigger deactivation of the heating element 14 by the device's control circuitry. In general, these operating aspects of the device may occur in accordance with established techniques. In particular, it will be appreciated the specific sensing technology underlying the operation of the sensor 8, and the manner in which the device responds to output signaling from the sensor 8, is not of fundamental significance to the principles underlying the present disclosure. What is significant is that an air path connecting from the mouthpiece end 18 to the inhalation sensor 8 bypasses the aerosol generation chamber 16, thereby reducing the risk of liquid leaking into the sensor chamber 10 and damaging the sensor 8 as compared to conventional air path configurations, such as represented in FIG. 1. Accordingly, the operation of the sensor 8 itself, and the manner in which the sensor's output signals are processed to determine whether or not the heating element 14 should be activated/deactivated, may be in accordance with any conventional approaches.

It may be noted the FIG. 2 implementation depicts the aerosol delivery device 1 as comprising a sensor chamber air inlet 32 that is provided so as to allow air from the environment to enter the sensor chamber 10 when a user inhales on the mouthpiece end 18 of the device 1. In this case, air can flow through the sensor chamber 10.

Thus to summarize the approach represented in FIG. 2, the device includes two air channels, the primary air channel 3 and the secondary air channel 5, that provide for separated fluid communication between the mouthpiece end of the device and the aerosol source (or liquid reservoir 12/aerosol generation chamber 16) and the sensor 8 respectively. It will be noted the sensor 8 is further from the mouthpiece end than the aerosol generation chamber 16 such that the secondary air channel 5 connecting from the mouthpiece end 18 to the sensor 8 bypasses the aerosol generation chamber 16. Because the secondary air channel 5 is arranged to bypass the aerosol generation chamber 16 there is less chance of the liquid entering the secondary air channel 5 and reaching the sensor chamber 10 containing the sensor 8, thereby helping to reducing the possibility of corrosion or damage to the sensor 8. This approach can therefore help increase the lifetime of the sensor 8 or reduce the regularity of maintenance required to maintain the sensor 8 in a working condition.

In the example of FIG. 2, the primary and secondary air channels 3, 5 are not connected or joined to one another within the device 1, that is to say the secondary air channel 5 is completely separate from and does not connect to the primary air channel 3. However, as discussed further below, in other implementations the secondary air channel may join the primary air channel at a location which is downstream of the aerosol generation chamber (i.e. between the aerosol generation chamber and the mouthpiece end). That is to say, the two air channels may not be completely separate within the device, but the air channel to the sensor may nonetheless be arranged to bypass (i.e., pass alongside) the aerosol generation chamber to help reduce the risk of liquid leaking from the aerosol generation chamber flowing upstream direction to contact the sensor 8.

FIG. 3 depicts an alternative embodiment of the aerosol delivery device 31. The aerosol delivery device 31 of FIG. 3 includes various components which are functionally similar to, and will be understood from, the description of corresponding elements described above in relation to FIG. 2 and identified by like reference signs.

In the device of FIG. 3, the air inlet 20 is positioned at the outer surface of the reusable part 2, unlike in FIG. 2 where it is positioned at the outer surface of the detachable/replaceable cartridge part 4.

In such a case, the air inlet 20 communicates with the first primary air channel portion 22 disposed in the detachable part 4 via third primary air channel portion 34 of the reusable part 2. The third primary air channel portion 34 comprises an opening 34a at the surface of the reusable part 2 that contacts the detachable part 4 when the two are coupled, i.e., at the interface surface. Likewise, the first primary air channel portion 22 comprises an opening 22a that is provided at the interface surface of the detachable part 4 that contacts the reusable part 2 when the two are coupled. Accordingly, when the reusable and detachable parts 2, 4 are coupled, the opening 34a and the opening 22a are arranged to be in fluid communication with each other, meaning that air from the environment is able to pass through the air inlet 20, third primary air channel portion 34, opening 34a, opening 22a, and first primary air channel portion 22 to the aerosol generation chamber 16. The remaining path for the air flow is as described with respect to the embodiment of FIG. 2. The third primary air channel portion 34 of the reusable part 2 may be isolated or sealed from any electrical components disposed in the reusable part 2. This may help in further preventing escaped liquid from interfering with any electronic components of the reusable part 2, not just the electrical components associated with the sensor 8.

The embodiment of FIG. 3 also shows the primary air channel 3 and the secondary air channel 5 being connected or joined at a location 36 downstream of the aerosol generation chamber 16 but prior to the opening 24a at the mouthpiece end 18. That is, within the device 1, the secondary air channel 5 may join with the primary air channel 3 at a location between the aerosol generation chamber 16 and the mouthpiece end 18. This may be advantageous when considering what the user is presented with at the mouthpiece end 18; that is, in FIG. 3 a single opening through which the user inhales is presented to the user, whereas in FIG. 2 the user is presented with at least two openings.

In the configuration of FIG. 3, escaped liquid cannot readily enter the sensor chamber 10 and sensor 8. For example, if the device 31 is stored or held such that the mouthpiece end 18 is the lowermost part of the device 31, then escaped liquid will flow generally downwards along primary air channel 3 and out opening 30 of the mouthpiece end 18. If, alternatively, the device 31 is held or stored such that the reusable part 2 is the lowermost part, then escaped liquid will flow generally along the first primary air channel portion 22, the third primary air channel portion 34, and out of air inlet 20. This configuration may be advantageous as it may save space within the device 31 because the primary and secondary air channels 3, 5 make use of a common section of the primary and secondary air channels 3, 5.

Moreover, FIG. 3 shows the sensor chamber 10 in fluid communication only with the second primary air channel portion 26. That is, the sensor chamber 10 of FIG. 3 is not provided with a sensor chamber air inlet 32. In this arrangement, the sensor 8 is configured to detect a change in pressure but air does not flow past the sensor 8. This can reduce the possibility of contaminating the sensor 8 or sensor chamber 10 with contaminants contained in air from the environment. This may also help prevent liquid ingress from the environment, e.g., in conditions such as rain, from damaging the sensor 8.

FIG. 4 depicts an alternative embodiment of the aerosol delivery device 41. The aerosol delivery device 41 of FIG. 4 includes various components which are functionally similar to, and will be understood from, the description of corresponding elements described above in relation to FIGS. 2 and 3 and identified by corresponding reference signs.

The device 41 of FIG. 4 differs from the device of FIG. 2 in comprising a removable mouthpiece cap 44 which covers a replaceable cartridge part 4a for use, wherein a secondary air channel 5 connecting from the mouthpiece end 18 to the inhalation sensor 8 is at least partly defined by a gap between the replaceable cartridge part 4a and the mouthpiece cap 44. The cartridge part 4a includes the aerosol source, i.e., the liquid reservoir 12, optional wicking material, and the heating element 14, as well as the aerosol generation chamber 16.

The cartridge part 4a includes the primary air channel 3 that extends through a central part thereof. This arrangement allows for fluid communication between the aerosol generation chamber 16 and the mouthpiece end 18 of the mouthpiece cap 44 via opening 24a provided at a first end of the cartridge part 4a. In the configuration shown, the cartridge part 4a includes the first primary air channel portion 22 which provides fluid communication between opening 22a positioned at a second end of the cartridge part 4a, opposite the first end, that interfaces with the reusable part 2.

The cartridge part 4a may be coupled to the reusable part 2 by any means as previously described above, such as a snap-fit arrangement. In much the same way as shown in FIG. 3, the opening 22a communicates with the opening 34a of the third primary air channel portion 34 of the reusable part 2 which communicates with the air inlet 20 provided at an external surface of the reusable part 2.

The mouthpiece cap 44 comprises the mouthpiece end 18 and includes an opening 30 to allow the user of the device 41 to inhale through the device 41. The mouthpiece cap 44 is configured to receive at least a part of the cartridge 4a in an inner volume of the mouthpiece cap 44. In other words, the mouthpiece cap 44 is configured to cover at least a portion of the cartridge part 4a. In one example, the mouthpiece cap 44 may be cylindrical or substantially cylindrical in shape with an opening 28a at an end opposite the opening 30. The opening 28a has a diameter larger than the part of the cartridge part 4a that is received in the inner volume of the mouthpiece cap 44. In this way, when the cartridge part 4a is coupled to the reusable part 2, the mouthpiece cap 44 can be placed over the cartridge part 4a and engage with the reusable part 2, which may include engagement at a peripheral portion of the reusable part 2 in a snap-fit manner.

FIG. 4 also shows the sensor 8 and sensor chamber 10 positioned in the reusable part 2 as described hereinbefore. The optional first secondary air channel portion 26 and opening 26a may also be provided. In this embodiment, either the opening 26a or the opening 10a can be arranged at a peripheral portion of the reusable part 2 such that it is not blocked by the cartridge part 4a when the cartridge part 4a is coupled to the reusable part 2. In other words, in the absence of the mouthpiece cap 44, the opening 26a or opening 10a is exposed to the environment.

Accordingly, the inner surface of the mouthpiece cap 44 is configured so as to at least partially define the secondary air channel 5. When the mouthpiece cap 44 is coupled to the reusable part 2, a gap exists between the outer surface of the cartridge part 4a and the inner surface of the mouthpiece cap 44. This gap fluidly communicates with the opening 26a and/or opening 10a, and hence the sensor 8, to define the secondary air channel 5. The secondary air channel 5 may terminate at the opening 30 of the mouthpiece end 18 of the device 1.

In use, the user may inhale on the mouthpiece end 18 of the mouthpiece cap 44 which causes air from the environment to pass from the air inlet 20, through the primary air channel 3, and into the user's mouth through opening 30. At the same time, air within the gap between the outer surface of the cartridge 4a and the inner surface of the detachable part 44 can be drawn along the inner surface of the detachable part 44 towards the opening 30 (that is, along secondary air channel 5). The sensor 8 may respond to the change in pressure at the mouthpiece end 18 caused by a user inhaling on the device 41 to activate/deactivate the heating element 16 as discussed above in accordance with broadly conventional techniques.

In one embodiment, the primary air channel 3 is provided in the cartridge part 4a while the secondary air channel 5 is provided in the mouthpiece cap 44. The primary air channel 3 may connect to or join the secondary air channel 5 at a portion downstream of the aerosol source, i.e., liquid reservoir 12. However, other arrangements are possible; for example, the cartridge part 4a may extend up to the mouthpiece end 18 of the detachable part 44 and be sealed thereto (by an O-ring or the like). In this case, a plurality of openings 30 may be provided at the mouthpiece end 18 of the mouthpiece cap 44 to independently communicate with the secondary air channel 5 and the primary air channel 3.

It should therefore be appreciated that the present disclosure provides a configuration of primary and secondary air channels 3, 5 that may help reduce or prevent leaked liquid from coming into contact with the sensor 8. The secondary air channel 5 may be said to bypass the aerosol generation chamber 16 (and/or the liquid reservoir 12). Accordingly, the sensor 8 stands less chance of damage or corrosion from leaked liquid flowing to the sensor 8 and may therefore experience a longer operational life. In some instances, this may make the installation of more improved or sensitive sensors 8 within the reusable part 2 more economically viable, thereby improving the user's experience when using the aerosol delivery device 1.

While FIGS. 2, 3 and 4 show exemplary implementations of the primary and secondary air channels 3, 5, it should be understood that many different configurations are also possible. For example, in both FIGS. 2 and 3, the secondary air channel 5 may be situated at, or substantially at, a peripheral portion of the detachable part 4, i.e., not coaxial with the longitudinal axis of the detachable part 4. However, the secondary air channel 5 may be provided with the opening 28a coaxially with the longitudinal axis of the detachable part 4. This may be particularly beneficial for backwards compatibility with other reusable parts such as, for example, reusable part 102 of FIG. 1. In such an embodiment, the air inlet 20 and first primary air channel portion 22 may be adjusted to accommodate the centrally located opening of the secondary air channel 5.

The disclosure also provides a detachable part 4 to be used with a reusable part 2. Indeed, for a user to change the vapor that is produced (e.g., flavor, concentration, or nicotine based or not) or to replace the liquid reservoir 12 if it has run dry, the user simply replaces the detachable part 4 with another detachable part 4. The detachable part 4 may be provided with features, such as knurling, on an outer surface thereof to aid in (un)screwing or (de)coupling the detachable part 4 from/to the reusable part 2.

It may also be appropriate to configure or design the primary and secondary air channels 3, 5 with certain characteristics, particularly when considering the use of certain types of sensor 8. For instance, when using a sensor that cannot readily be calibrated for sensitivity, such as a microphone sensor, it may be helpful to configure the primary and secondary air channels 3, 5 so as to have similar or identical draw resistances. This helps to ensure that the pressure drop detected by the sensor is based on the air flow entering the heater chamber 16. In such a case, the draw resistance of each channel 3, 5 should be approximately half of the total draw resistance, e.g., for a total draw resistance of 784 Pa (80 mmWG) each channel should have a draw resistance of 392 Pa (40 mmWG). Draw resistance is usually defined in millimeters of Water Gauge (mmWG) measured at a standard flow rate of 17.5 mL/s. However, these requirements on draw resistances may be less significant when using a digital pressure sensor as the sensor 8 as such digital pressure sensors can usually be calibrated for sensitivity.

Thus, there has been described an aerosol delivery device that includes a mouthpiece end and an aerosol generation chamber in fluid communication with the mouthpiece end via a primary air channel. The aerosol generation chamber includes an aerosol source for generating an aerosol from a source material for inhalation by a user through the mouthpiece end during use. The aerosol delivery device also includes a sensor for detecting when a user inhales on the mouthpiece end. The sensor is in fluid communication with the mouthpiece end via a secondary air channel, and the sensor is located further from the mouthpiece end than the aerosol source. The secondary air channel bypasses the aerosol generation chamber. There has also been described an aerosol delivery device comprising an aerosol source for generating an aerosol from a source material for user inhalation through a mouthpiece end of the device, and a sensor for sensing when a user inhales on the mouthpiece end. The aerosol delivery device is formed of a reusable part and a replaceable cartridge part, wherein the reusable part includes the sensor and the replaceable cartridge part includes the source material and the mouthpiece end, and wherein the replaceable part further includes a primary air channel for providing fluid communication between the aerosol source and the mouthpiece end of the device and a secondary air channel providing fluid communication between the sensor and the mouthpiece end when the replaceable cartridge is coupled to the reusable part in use.

While the above described embodiments have in some respects focused on some specific example aerosol provision systems/aerosol delivery systems, it will be appreciated the same principles can be applied for aerosol provision systems using other technologies. That is to say, the specific manner in which various aspects of the aerosol provision system function are not directly relevant to the principles underlying the examples described herein.

In order to address various issues and advance the art, the entirety of this disclosure shows by way of illustration various embodiments in which the claimed invention(s) may be practiced and provide for superior aerosol delivery devices and replaceable cartridge parts that comprise a primary air channel for providing fluid communication between an aerosol source for generating aerosol from a source material for user inhalation and a mouthpiece end, and a secondary air channel for providing fluid communication between a sensor and mouthpiece end. The advantages and features of the disclosure are of a representative sample of embodiments only, and are not exhaustive and/or exclusive. They are presented only to assist in understanding and to teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. An aerosol delivery device comprising:
a mouthpiece end;
a primary air channel extending from an air inlet for the aerosol delivery device to an opening in the mouthpiece end;
an aerosol generation chamber in fluid communication with the mouthpiece end via a portion of the primary air channel, wherein the aerosol generation chamber comprises an aerosol source for generating an aerosol from a source material for inhalation by a user through the mouthpiece end during use; and
a sensor for detecting when a user inhales on the mouthpiece end, wherein the sensor is in fluid communication with the mouthpiece end via a secondary air channel, and wherein the sensor is located further from the mouthpiece end than the aerosol source, and the secondary air channel bypasses the aerosol generation chamber such that the secondary air channel is separate from the primary air channel up to a location in the primary air channel which is downstream of the aerosol generation chamber.

2. The aerosol delivery device of claim 1, wherein the secondary air channel does not connect with the primary air channel within the aerosol delivery device.

3. The aerosol delivery device of claim 1, wherein the secondary air channel connects with the primary air channel at a location between the aerosol generation chamber and the mouthpiece end.

4. The aerosol delivery device of claim 1, wherein the aerosol delivery device is provided with a sensor air inlet in fluid communication with the sensor so that when a user inhales on the mouthpiece end, air is drawn in through the sensor air inlet, past the sensor and along the secondary air channel towards the mouthpiece end.

5. The aerosol delivery device of claim 1, wherein the aerosol delivery device comprises a first part that includes the mouthpiece end and the aerosol generation chamber and a second part that includes the sensor, wherein the first part and second part are detachable from one another, wherein the secondary air channel provides fluid communication between the sensor and the mouthpiece end across an interface between the first part and second part when the first part and second part are coupled together for use.

6. The aerosol delivery device of claim 5, wherein the first part comprises a cartridge containing the source material, and wherein the secondary air channel is formed within the cartridge.

7. The aerosol delivery device of claim 5, wherein the first part comprises a cartridge part containing the source material and a separable mouthpiece cap covering at least a portion of the cartridge part, and wherein at least a part of the secondary air channel is formed by a gap between the cartridge part and the separable mouthpiece cap.

8. The aerosol delivery device of claim 5, wherein the primary air channel extends between an air inlet and the mouthpiece end.

9. The aerosol delivery device of claim 8, wherein the air inlet is provided at the interface between the first part and second part.

10. The aerosol delivery device of claim 8, wherein the air inlet is provided in the first part.

11. The aerosol delivery device of claim 8, wherein the air inlet is provided in the second part.

12. The aerosol delivery device of claim 1, wherein the sensor is a pressure sensor configured to sense a drop in pressure in the secondary air channel when a user inhales on the mouthpiece end of the aerosol delivery device.

13. The aerosol delivery device of claim 1, wherein the primary and secondary air channels are configured to have comparable draw resistances.

14. The aerosol delivery device of claim 1, wherein the aerosol delivery device is formed of a reusable part and a replaceable cartridge part, and wherein the reusable part includes the sensor and the replaceable cartridge part includes the source material and the mouthpiece end, and wherein the replaceable part further includes the primary air channel for providing fluid communication between the aerosol source and the mouthpiece end of the aerosol delivery device and the secondary air channel for providing fluid communication between the sensor and the mouthpiece end when the replaceable cartridge is coupled to the reusable part in use.

15. An aerosol delivery device comprising:
a mouthpiece end;
a primary air channel extending from an air inlet for the aerosol delivery device to an opening in the mouthpiece end;
an aerosol generation chamber in fluid communication with the mouthpiece end via a portion of the primary air channel, wherein the aerosol generation chamber comprises aerosol generation means for generating an aerosol from a source material for inhalation by a user through the mouthpiece end during use; and
sensor means for detecting when a user inhales on the mouthpiece end, wherein the sensor means is in fluid communication with the mouthpiece end via a secondary air channel, and wherein the sensor means is located further from the mouthpiece end than the aerosol generation means, and the secondary air channel bypasses the aerosol generation chamber such that the secondary air channel is separate from the primary air channel up to a location in the primary air channel which is downstream of the aerosol generation chamber.

* * * * *